United States Patent [19]

Sandow et al.

[11] Patent Number: 5,565,423
[45] Date of Patent: Oct. 15, 1996

[54] CYCLOPEPTIDES AND THEIR USE AS ABSORPTION PROMOTERS WHEN APPLIED TO THE MUCOSA

[75] Inventors: Jürgen Sandow, Glashütten/Taunus; Walter Dürckheimer, Hattersheim am Main; Günter Ditzinger, Frankfurt am Main, all of Germany; Hans-Peter Merkle, Zürich, Switzerland

[73] Assignee: Hoechst Aktiengesellschaft, Frankfurt am Main, Germany

[21] Appl. No.: 418,882

[22] Filed: Apr. 7, 1995

Related U.S. Application Data

[63] Continuation of Ser. No. 65,013, May 24, 1993, abandoned.

[30] Foreign Application Priority Data

May 26, 1992 [DE] Germany .......................... 42 17 350.7

[51] Int. Cl.⁶ .................................................. A61K 38/12
[52] U.S. Cl. .................... 514/11; 514/2; 514/9; 530/317
[58] Field of Search ............... 514/2, 9, 11; 530/317, 530/318, 319, 320

[56] References Cited

U.S. PATENT DOCUMENTS

| | | | |
|---|---|---|---|
| 3,817,973 | 6/1974 | Bouchaudon et al. | 530/319 |
| 5,091,365 | 2/1992 | Sandow et al. | 514/9 |
| 5,177,059 | 1/1993 | Handley et al. | 530/317 |

FOREIGN PATENT DOCUMENTS

| | | | |
|---|---|---|---|
| 0302466 | 2/1989 | European Pat. Off. | |
| 2204887 | 9/1972 | Germany . | |
| 0005709 | 2/1971 | Japan | 530/317 |

*Primary Examiner*—Howard E. Schain
*Attorney, Agent, or Firm*—Finnegan, Henderson, Farabow, Garrett & Dunner, L.L.P.

[57] ABSTRACT

Cyclopeptides and their use as absorption promoters when applied to the mucosa

The invention relates to a compound of the formula I

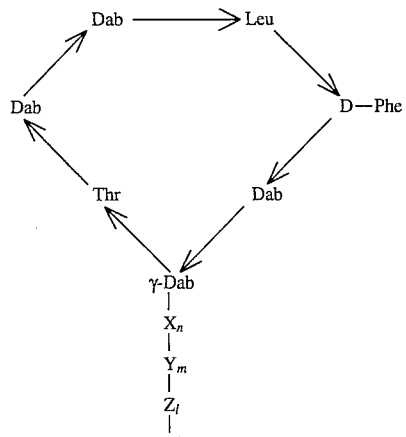

or a physiologically tolerated salt thereof, (I)

in which X is a basic L- or D-amino acid,
Y is a neutral or basic L- or D-amino acid,
Z is a neutral or basic L- or D-amino acid, which can be identical to or different from Y,
$R^1$ is an N-bonded acyl radical of the formula II

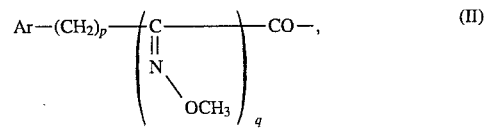

in which Ar is a phenyl radical, which is optionally substituted by 1, 2 or 3 identical or different radicals from the series comprising hydroxyl, ($C_1$–$C_4$)-alkoxy, amino, carboxyl, ($C_1$–$C_4$)-alkylamino and halogen, or is a 2-aminothiazol-4-yl radical, p is an integer from zero to 4 and q, n, m and l independently of one another are zero or 1.

The invention additionallly relates to the use of compounds of the formula I and physiologically tolerated salts thereof for promoting the absorption of peptides and proteins when applied to the mucosa, and pharmaceutical formulations which contain a pharmacologically active amount of one or more peptides or proteins and a compound of the formula I or physiologically tolerated salts thereof.

8 Claims, No Drawings

CYCLOPEPTIDES AND THEIR USE AS ABSORPTION PROMOTERS WHEN APPLIED TO THE MUCOSA

This application is a continuation of application Ser. No. 08/065,013, filed May 24, 1993, now abandoned.

DESCRIPTION

The invention relates to cyclopeptides and their use for promoting the absorption of peptides and proteins when applied to the mucosa.

The use of peptides and proteins as medicaments is made considerably more difficult by the problems of a suitable pharmaceutical formulation from which the peptide or protein to be used therapeutically or diagnostically is absorbed in an adequate amount and reliably.

The administration of one or more daily individual doses by nasal application, either in the form of nose drops or by spraying a suitable solution into the nose, is known [J. Sandow, W. Petri (1985), Transnasal Systemic Medications, Verlag Elsevier, 183–199]. Readily tolerated aqueous solutions with added preservatives and if appropriate auxiliaries to increase the absorption are used for this. The customary auxiliaries for increasing absorption (absorption enhancers) all irritate the mucosa or are unsuitable due to an unpleasant smell or taste, and often already lead to considerable pain and lacrimation after a single application, or generate a progressive irritation and inflammation of the nasal mucosa after several applications. This applies, for example, to derivatives of fusidic acid, to bile acids, to surfactants and to the various glycols (polyethylene glycol, polypropylene glycol). The use of cyclopeptides based on naturally occurring substances for promotion of the absorption of peptides and proteins on application to the mucosa is furthermore described in EP-B-0 302 466. These cyclopeptides are a mixture of chemically similar compounds; they must therefore be purified for pharmaceutical use. Above all, they have an intrinsic antibiotic activity, which may lead to the development of resistance in certain germs.

The object is therefore to provide compounds which improve the spectrum of action of peptides and proteins employed as pharmaceuticals by effecting, with good tolerability and lack of antibiotic partial action, good promotion of absorption.

According to the invention, this object is achieved by compounds of the formula I

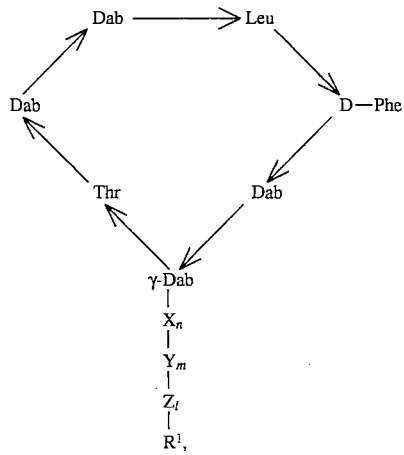

and physiologically tolerated salts thereof, in which X is a basic L- or D-amino acid, Y is a neutral or basic L- or D-amino acid, Z is a neutral or basic L- or D-amino acid, which can be identical to or different from Y, $R^1$ is an N-bonded acyl radical of the formula II

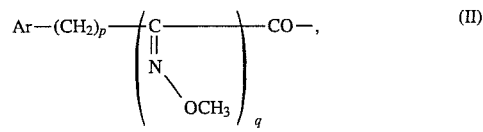

in which Ar is a phenyl radical, which is optionally substituted by 1, 2 or 3 identical or different radicals from the series comprising hydroxyl, $(C_1-C_4)$-alkoxy, amino, carboxyl, $(C_1-C_4)$-alkylamino and halogen, or is a 2-aminothiazol-4-yl radical, p is an integer from zero to 4 and q, n, m and 1 independently of one another are zero or 1.

Those radicals X, Y and Z which are derived from naturally occurring amino acids (cf., for example, Schröder, Lübke, The Peptides, Volume 1, New York 1965) and 2,4-diaminobutyric acid (Dab), antipodes thereof and simple metabolites, which, if they are chiral, can be present in the D- or L-form, are preferred. γ-Dab is 2,4-diaminobutyric acid linked to the ring via the γ-amino group.

Unless stated otherwise, the three-letter symbols (cf., for example, Pure Appl. Chem. 56 (1984) 595–624 and Eur. J. Biochem. 138 (1984) 9–37) for the radicals of the amino acids are used. These symbols are preceded by the symbol "D" if the radical is the radical of a D-amino acid; radicals without a configuration symbol have the L configuration.

The invention relates both to the optically pure compounds and to stereoisomer mixtures, such as enantiomer mixtures and diastereomer mixtures.

Compounds of the formula I which are preferably employed are those in which

X is lysine, ornithine, 2,4-diaminobutyric acid or arginine,

Y and Z independently of one another are lysine, ornithine, 2,4-diaminobutyric acid, arginine, threonine or serine and $R^1$, n, m and 1 have the abovementioned meaning, it being possible for the amino acids each to be present in the D- or L-form.

The following compounds are especially preferred:

Peptide PMB-1:

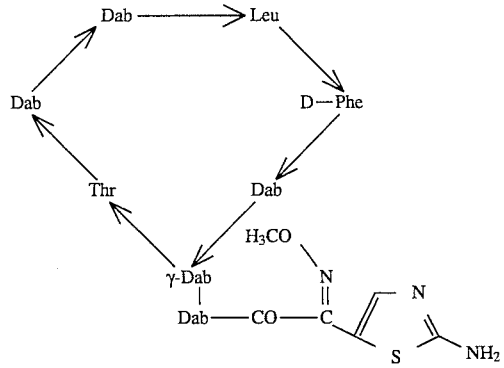

Peptide PMB-II:

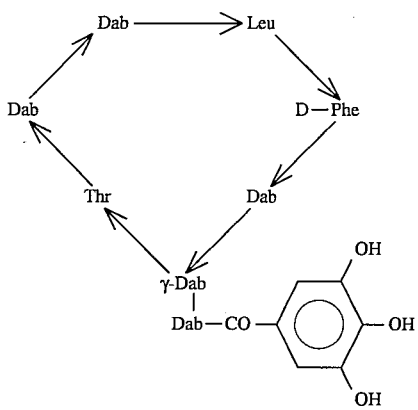

Peptide PMB-III:

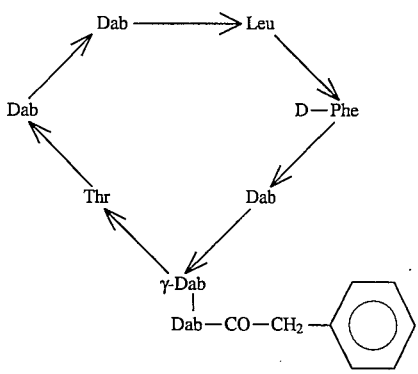

The compounds according to the invention are prepared, for example, using the general methods of peptide chemistry (Houben-Weyl, Methoden der organischen Chemie (Methods of organic chemistry), 15/1 and 2). The compounds can be prepared, for example, in stages starting from polymyxin B heptapeptide (formula I:1=m=n=0; $R^1$=H), or from polymyxin B octapeptide (formula I:1=m=0; $X_n$=L-Dab; $R^1$=H) or from polymyxin B nonapeptide (formula I:1=0, $Y_m$=L-Thr; $X_n$=L-Dab; $R^1$=H), the amino groups of which, with the exception of that to be acylated, are protected, and the corresponding activated carboxylic acids (for example carboxylic acid halides, mixed anhydrides or active esters).

The starting peptides can be obtained by reductive cleavage of N-Boc-protected polymyxin B, for example using metal hydrides, for example $NaBH_4$ or $NaCNBH_3$, or by enzymatic cleavage, for example with the protease ficin, which is known from the literature. In this case, the N-oxidopyridyl-methoxycarbonyl protective group has proved to be a suitable N-protective group.

The invention furthermore relates to the use of compounds of the formula I for promoting the absorption of peptides and proteins on application to the mucosa. The compounds according to the invention help quite considerably to improve the absorption of peptides and proteins on application to the mucosa. The increase in the activity (based on improved absorption) of the peptides or proteins after addition of the compounds according to the invention is thus 300 to 400%, and can be more than 1000% in an individual case.

The compounds according to the invention moreover cause no pain sensation and damage to the mucosa in humans following nasal application of 1 to 200 µl of a concentration of $10^{-5}$ to $10^{-1}$ mol/l. Local use of the same concentration through vaginal, rectal or buccal medicament forms (i.e., for example, films, tablets or suppositories) also leads to no irritation of the mucosa.

For most of the peptides and proteins known today which are used or will shortly be used as therapeutics or diagnostics, application to the mucosa, such as, for example, nasal, buccal, rectal, vaginal or pulmonal use, but in particular nasal, is appropriate and possible.

Peptides and proteins which are suitable for this are those which comprise 3 to 225 amino acids, such as, for example, TRH (protirelin, thyroliberin), LHRH (gonadoliberin), chemically modified peptide analogs of hypothalamic regulatory hormones, such as, for example, buserelin, somatostatin and cyclic somatostatin analogs, somatorelin, GRH analogs, peptide analogs of hypophysis hormones, such as, for example, the corticotropin analog alsactide (ACTH-17), calcium-regulating hormones (calcitonin, parathormone) and their analogs, as well as gastrointestinal hormones (for example secretin and cholecystokinin) and pancreatic hormones (insulin and insulin analogs). Those having 3 to 51 amino acids are particularly suitable.

The following may be mentioned in particular:

| Name of the peptide or protein | Use, for example for: | Number of amino acids |
|---|---|---|
| Oxytocin | uterine inertia | 9 |
| Vasopressin | diabetes insipidus | 9 |
| Ornipressin | hemorrhages | 9 |
| Desmopressin | diabetes insipidus | 9 |
| Corticotripin (ACTH) | inflammatory diseases | 39 |
| Tetracosactide | inflammatory diseases | 24 |
| Alsactide | " | 17 |
| Insulin | diabetes mellitus | 51 |
| beta-sleep ind. Peptide | sleep disturbances | 9 |
| Secretin | gastric hemorrhages | 27 |
| Cholecystokinin | diseases of the biliary tract, as an appetite suppressant | 8–32 |
| Somatoliberin (GRH) | retarded growth | 44 |
| [D-Ala2]Somatoliberin-(1-29)-amide | " | 29 |
| Somatoliberinyl-glycine | " | 45 |
| Glucagon | hypoglycemia | 29 |
| Somatostatin | gastric hemorrhages | 14 |
| Octreotide | tumors | 8 |
| Spantide | substance P inhibition | 11 |
| Corticoliberin (CRF) | hypophysis diagnostic | 41 |
| Bradykinin antagonists | allergic and inflammatory disorders | 9–11 |
| Atriopeptin III | cardiac and renal insufficiency | 24 |
| ANF-(99-126) | " | 28 |
| Thymopentin | rheumatoid arthritis | 5 |
| Interferon-alpha | colds | 125 |
| Thyroliberin (TRH) | hypophysis diagnostic | 3 |
| Gonadoliberin (LHRH) | cryptorchism, sterility | 10 |
| Buserelin | prostate cancer, endometriosis | 9 |
| Goserelin | prostate cancer, endometriosis | 10 |
| Triptorelin | prostate cancer, endometriosis | 10 |
| LH-RH-T | prostate cancer, endometriosis | 9 |
| Leuprorelin | prostate cancer, endometriosis | 9 |

-continued

| Name of the peptide or protein | Use, for example for: | Number of amino acids |
|---|---|---|
| Lutrelin | prostate cancer, endometriosis | 9 |
| Nafarelin | prostate cancer, endometriosis | 10 |
| Histrelin | prostate cancer, endometriosis | 9 |
| Calcitonin | Paget's disease, osteoporosis | 32 |
| Elcatonin | Paget's disease, osteoporosis | 32 |
| Parathormone-(1-34) | hypocalcemia | 34 |
| Sincalide | diagnostic for pancreatic function | 8 |
| Ceruletide | " | 10 |
| Pentagastrin | diagnostic for gastric function | 5 |
| Desglugastrin | " | 7 |
| Ociltide | intestine-contracting | 5 |
| Angiogenin | tissue regeneration | 123 |
| TGF-beta | tumor therapy, immunosuppression | 224 |
| Hirudine | inhibition of coagulation | 64, 65 |
| GM-CSF | stimulation of bone marrow | 127 |
| Erythropoietin | antianemic agent | 165 |

These peptides and proteins can be obtained by generally known processes, for example by Merrifield synthesis, genetic engineering and by isolation of naturally occurring peptides and proteins.

The invention furthermore relates to pharmaceutical formulations comprising a) a pharmacologically active amount of one, two or three peptides or proteins in each case comprising 3 to 225 amino acids, in particular 3 to 51 amino acids or physiologically tolerated salts thereof, and b) at least one auxiliary of the formula I.

Preferred formulations are those which comprise an auxiliary of the formula I in which X is lysine, ornithine, 2,4-diaminobutyric acid (Dab) or arginine, Y and Z independently of one another are lysine, ornithine, 2,4-diaminobutyric acid, arginine, threonine or serine and $R^1$, n, m and l have the abovementioned meaning, it being possible for the amino acids each to be present in the D- or L-form.

Especially preferred formulations are those which comprise at least one auxiliary chosen from the peptides PMB-I to -III.

The pharmaceutical formulations according to the invention furthermore preferably comprise a peptide or protein comprising 3 to 225 amino acids, in particular a peptide or protein comprising 3 to 51 amino acids.

However, formulations containing two or three different peptides and/or proteins, such as, for example, corticotropin+LHRH+GRH, or protirelin+LHRH+GRH, in combination with at least one auxiliary of the formula I, are also of interest, in particular for use as a diagnostic.

The dose of the peptides and/or proteins and of the auxiliaries of the formula I in the formulations or products according to the invention when used on mammals, preferably on humans, is in the range from 10 μg to 10 mg per peptide/protein and use, and, for the auxiliary of the formula I, is at a concentration of $10^{-5}$ to $10^{-1}$ mol/l per use, preferably between $10^{-4}$ and $10^{-2}$ mol/l.

The formulations according to the invention can be used by application to the mucosa, i.e. nasally, buccally, rectally, pulmonarily or vaginally. Nasal application is preferred here.

The pharmaceutical formulations according to the invention can be prepared by the method known to the person skilled in the art with addition of excipients suitable for the production of pharmaceutical preparations. Pharmaceuticals are especially suitable for application to the mucosa, such as, for example, tablets, suppositories, capsules, gels, films, emulsions, suspensions, aerosols, solutions or sprays (Sucker, Fuchs, Speiser, Pharmazeutische Technologie (Pharmaceutical Technology), Georg Thieme Verlag 1978).

The following are preferably used:

1. Aqueous or aqueous-alcoholic solutions for application with a dropper pipette or a plastic squeeze bottle, or for nebulization with a metered nebulizer pump.

In addition to the active compound and the absorption promoter, the formulation can for example comprise an isotonicizing additive, for example sodium chloride, potassium nitrate or potassium sodium phosphate, polyalcohols, such as, for example, glucose, mannitol or sorbitol, buffer substances, such as, for example, potassium sodium phosphate, citric acid and its salts and mixtures of the two, in order to establish a pH range from 3 to 8, a preservative, for example benzalkonium chloride, benzyl alcohol, 1,1,1-trichloro-2-methyl-2-propanol or methyl 4-hydroxybenzoate, a chelating agent, for example sodium EDTA, and, as the solvent, water or mixtures of water with $(C_1-C_4)$-alkanols. The solution is applied with a suitable apparatus or sprayed into the nose or onto the oral mucosa.

2. Aqueous or aqueous-alcoholic gels for introduction into body cavities (mouth, nose, rectum, vagina)

In addition to 1., a gel comprises an additive which increases the viscosity, for example a polyacrylate polymer or a cellulose ether, such as, for example, hydroxypropylmethylcellulose (HPMC), hydroxyethylcellulose (HEC) or methylhydroxyethylcellulose (MHEC).

3. Suspensions in propellent gases

In addition to the micronized active compound and the micronized absorption promoter, the formulation can comprise, as a propellent gas, a chlorofluorohydrocarbon, for example ®Frigen F 11, 12 or 114 (®=a registered trademark of Hoechst AG), or mixtures thereof or a fluorohydrocarbon such as tetrafluoroethane (HFA 134a) or heptafluoropropane (HFA227) and a suspending auxiliary, for example sorbitan trioleate, oleic acid or lecithin. The containers are filled in a manner which is known per se by the low temperature filling process, or by filling under pressure.

4. Triturations with carrier auxiliaries filled into capsules for intranasal or inhalative use Hard gelatin capsules are filled with the micronized substances (active compound and absorption promoter), if appropriate after addition of an agent for improving the flow properties, such as lactose. The contents of one capsule is applied intranasally or pulmonarily with an inhalation aid which enables the powder to be converted into inhalable fumes.

5. Buccal forms

The active compound and absorption promoter can be present in dissolved or suspended form. Compressed articles or laminates of mixtures of the active compound and absorption promoter in polymers are suitable drug forms. Possible polymers are cellulose ethers (for example HPMC or carboxymethylcellulose (CMC)) or polyacrylates.

EXAMPLE 1

Synthesis of PMB-I 1.26 g (1 mmol) of "tetra-Boc-polymyxin B-octapeptide" are dissolved in 10 ml of pyridine, and 0.318 g of the HOBt ester (HOBt=1-hydroxybenzotriazole) of 2-amino-thiazol-4-yl-2-methoximinoacetic acid is added. After 24 hours, the pyridine is evaporated in vacuo, the residue is dissolved in 200 ml of ethyl acetate and the solution is washed first with 200 ml of N/10 hydrochloric acid and then with 200 ml of water. After drying over sodium sulfate, the solvent is removed, the residue is dissolved again in a mixture of ethyl acetate/methanol 85:15, and the solution is chromatographed with the same solvent mixture over a silica gel column (4×50 cm; 70–200 µm; 200 g). 40 fractions of 10 ml are collected. Fractions 21–35 contain the desired substance. The solvent is removed in vacuo on a rotary evaporator.

Yield of the intermediate: 1.1 g (76% of theory)

Molecular weight:1445 g/mol ($C_{65}H_{104}N_{16}O_{19}S$)

$R_f$ value [thin layer chromatography silica gel 60 F 254/Merck, Darmstadt, ethyl acetate/methanol 85:15]=0.51

Splitting off the Boc protective groups:

1.1 g of the intermediate are dissolved in 10 ml of trifluoroacetic acid, while cooling with ice, and the solution is then left to stand at room temperature for 2 hours. After concentration, the solid residue is triturated with ether, filtered off, rinsed with ether, and dried over $P_2O_5$ in vacuo.

Yield:0.96 g (78.2%)

Molecular weight:1046 g/mol ($C_{45}H_{72}N_{16}O_{11}S \times 5\ CF_3CO_2H$)

$R_f$ value [thin layer chromatography silica gel 60 F 254/Merck, Darmstadt, mobile phase n-butanol (50), pyridine (20), glacial acetic acid (6), water (24)]=0.11.

EXAMPLE 2

Synthesis of PMB-II 1.25 g (1 mmol) of "tetra-Boc-polymyxin B octapeptide" are dissolved in 10 ml of pyridine, and 0.287 g of the HOBt ester of gallic acid is added. After 48 hours, the pyridine is stripped off, the residue is dissolved in 200 ml of ethyl acetate and this solution is washed first with 200 ml of N/10 hydrochloric acid and then with 200 ml of water. After drying over sodium sulfate, the solvent is removed, the residue is dissolved again in a mixture of ethyl acetate/methanol (85:15), and the solution is chromatographed with the same solvent mixture. Silica gel (70–200 µm), which has been washed beforehand with half-concentrated hydrochloric acid to remove iron, and then with water until a neutral reaction is obtained, and dried at 130° C., is used as the carrier material. 40 fractions of 15 ml are eluted. Fractions 34–39 contain the desired substance. The solvent is removed in vacuo on a rotary evaporator.

Yield of the intermediate:0.89 g (62.8%)

Molecular weight=1414.58 g/mol.

Splitting off the Boc protective groups was carried out analogously to Example 1.

Yield:0.79 g (86%)

Molecular weight:1014 g/mol ($C_{46}H_{71}N_{13}O_{13} \times 4CF_3CO_2H$=1470.21)

$R_f$ value ( separation system as under Example 1):0.05.

EXAMPLE 3

Synthesis of PMB-III 1.26 g (1 mmol) of "tetra-Boc-polymyxin B octapeptide" are dissolved in 10 ml of pyridine, and 0.233 g (1 mmol) of the hydroxysuccinimide ester of phenylacetic acid is added. After a reaction time of 20 hours at room temperature, the residue is dissolved in 200 ml of ethyl acetate, and the solution is washed with 200 ml of N/10 hydrochloric acid and with 200 ml of water. After drying over sodium sulfate, the solvent is removed, the residue is dissolved again in a mixture of ethyl acetate/methanol (85:15), and the solution is chromatographed over a silica gel column (4×50 cm; 70–200 µm; 200 g) using the same solvent mixture. 40 fractions of 15 ml are removed. Fractions 20–39 contain the desired product ($C_{67}H_{105}N_{13}O_{18}$). The solvent is removed in vacuo on a rotary evaporator.

Yield of the intermediate:0.85 g (61.2%)

Molecular weight:1386 g/mol (Li salt)

$R_f$ value (thin layer chromatography as Example 1)=0.57

Splitting off the protective groups was carried out as in Example 1.

Yield:0.59 g (97.7%)

Molecular weight:980 g/mol ($C_{47}H_{73}N\_O_{10}$).

$R_f$ value (thin layer chromatography solvent mixture as in Example 1): 0.26

EXAMPLE 4

Investigation of the action of LHRH or LHRH analogs

A method which is suitable for demonstrating the intensification of action of a peptide or protein by means of a cyclopeptide according to the invention is, for example, determination of the release of LH in male rats (100 g body weight) anesthetized by ethyl carbamate. In this method, the hormone release is compared over a period of 6–7 hours after treatment, i.e. after nasal or rectal application of LHRH or LHRH analogs in physiological saline solution with or without addition of cyclopeptides of the formula I. It was found that, for example, a 21- to 32-fold increase in the action of a nasally administered dose of 10 ng buserelin is achieved by the peptides PMB-I to -III in a concentration of 0.01 M, based on the release of LH. The action of a nasally administered dose of 800 ng of LHRH was intensified by a factor of 3 to 6 by the peptides PMB-I to -III in the same animal model, also based on the areas under the curves.

EXAMPLE 5

Investigation of the Intensification of Action of ACTH

The action of cyclopeptides of the formula I on the absorption of ACTH (corticotropin) and ACTH analogs was investigated, after application of the test substances according to Example 4, on male rats (100 g body weight) anesthetized by phenobarbital or ether. The release of corticosterone was determined in the serum by specific radioimmunoassay as the parameter of the action. It was found that after nasal treatment, for example, with the ACTH analog alsactide (ACTH-17) in a dose of 1.5 µg in the presence of peptides (PMB-I to -III), the corticosterone release was increased 2- to 3-fold over 3 hours.

EXAMPLE 6

Investigation of the Intensification of Action of Calcitonin

The action of cyclopeptides of the formula I on the absorption of calcitonin and calcitonin analogs (for example salmon calcitonin) was investigated on male rats of 100 or 200 g body weight after application according to Example 4, by determination of the serum calcium level over a period of 1–6 hours after the treatment.

It was found that the action of a nasal dose of 1.2 μg of salmon calcitonin was increased 3.4-fold by addition, for example, of peptide PMB-I in a concentration of 0.01 M, based on the decrease in the serum calcium level.

EXAMPLE 7

Investigation of the Intensification of Action of insulin

The action of cyclopeptides of the formula I on nasal absorption of human insulin or other insulin was investigated, after application of the test substances according to Example 4, on male rats having a body weight of 100 g and anesthetized by ether. The decrease in the blood glucose level serves as a parameter for the action.

It was found that peptides PMB-I to -III in a concentration of 0.01 M were able to improve nasal absorption of 20 IU/kg of human insulin by a factor of 3–4.

EXAMPLE 8

Investigation of the Mucosa Tolerability

The tolerability of cyclopeptides of the formula I which are used as auxiliaries for increasing absorption can be tested on the isolated gastric mucosa of the guinea pig. [Wirth K, Bickel M & Deutschländer N (1987): Patent Blue permeation through the isolated guinea pig gastric mucosa: a quantitative method for the assessment of gastric irritants. Med. Sci. Res. 15, 881–882]. The bovine nasal mucosa is used in a similar model. [Ditzinger G, Sandow J, Merkle HP (1990): In vitro model for nasal peptide delivery: Enhancement effects of cyclopeptides on the transport rate of two oligopeptides. Proceed. Intern. Symp. Contr. Rel. Bioact. Mater. 17, 220–221]. The permeation of Patent Blue as a marker substance for mucosa damage was investigated using the latter model. While bile acids used as absorption enhancers, such as sodium deoxycholate or sodium glycocholate, or surfactants used as absorption enhancers, such as polydocanol (Laureth-9), increased the permeation of Patent Blue by about 300%, peptides PMB-I to -III show no influence on the rate of permeation.

EXAMPLE 9

Nasal Solution

| | |
|---|---|
| Buserelin | 0.15 mg |
| Peptide PMB-I | 1.50 mg |
| Sodium chloride | 0.80 mg |
| Citric acid · H$_2$O | 0.11 mg |
| Sodium citrate · 2H$_2$O | 0.15 mg |
| Benzalkonium chloride | 0.01 mg |
| Disodium EDTA | 0.01 mg |
| Water (purified) to | 0.1000 ml |

EXAMPLE 10

Gel

| | |
|---|---|
| Alsactide (ACTH-17) | 0.003 mg |
| Peptide PMB-II | 1.200 mg |
| Polyacrylic acid 940 | 0.400 mg |
| Sodium hydroxide solution, 15% strength | 0.900 mg |
| Glycerol | 15.000 mg |
| Methyl 4-hydroxybenzoate | 0.150 mg |
| Purified water to | 100.000 ml |

EXAMPLE 11

Suppository

| | |
|---|---|
| Salmon calcitonin | 0.200 mg |
| Peptide PMB-III | 1.000 mg |
| Suppository base (hard fat) to | 2.500 g |

EXAMPLE 12

Diagnostic

| | |
|---|---|
| Protirelin | 0.050 mg |
| Gonadoliberin | 0.025 mg |
| Somatoliberin | 0.025 mg |
| Peptide PMB-I | 0.250 mg |
| Citric acid · H$_2$O | 0.170 mg |
| Disodium monohydrogen phosphate · 12H$_2$O | 1.100 mg |
| Sodium chloride | 0.600 mg |
| Benzyl alcohol | 1.000 mg |
| Purified water to | 0.100 ml |

We claim:

1. A pharmaceutical formulation comprising a) a pharmacologically active amount of one, two or three peptides in each case comprising 3 to 51 amino acids, or physiologically tolerated salts thereof, and b) at least one additional peptide, said additional peptide being Peptide PMB-I:

Peptide PMB-II:
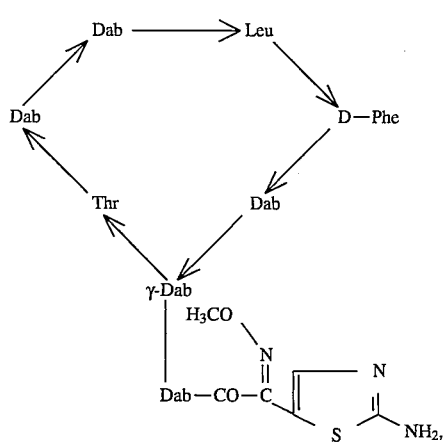
Peptide PMB-III:
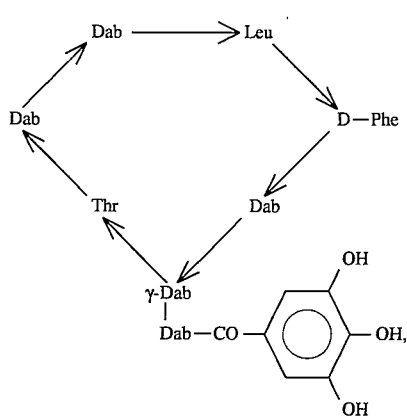
or a physiologically tolerated salt of any of said additional peptides.
2. At least one peptide, said peptide being a Peptide PMB-I:
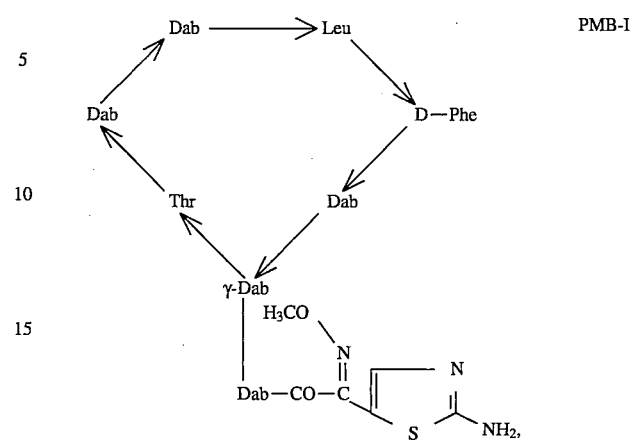
Peptide PMB-II:
Peptide PMB-III:
or a physiologically tolerated salt thereof.

3. The compound of the formula Peptide PMB-I:

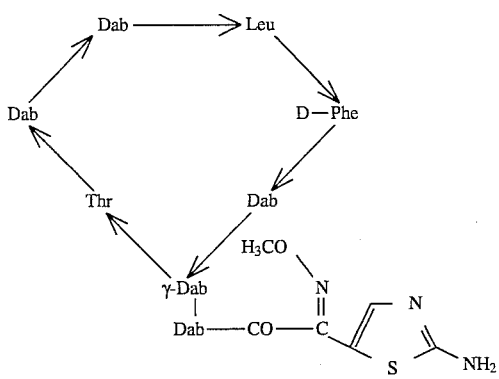

or a physiologically tolerated salt thereof.

4. The compound of the formula Peptide PMB-II:

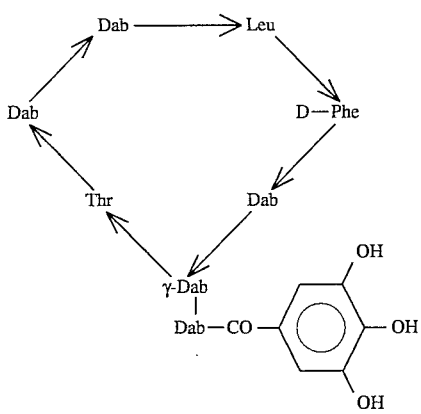

or a physiologically tolerated salt thereof.

5. The compound of the formula Peptide PMB-III:

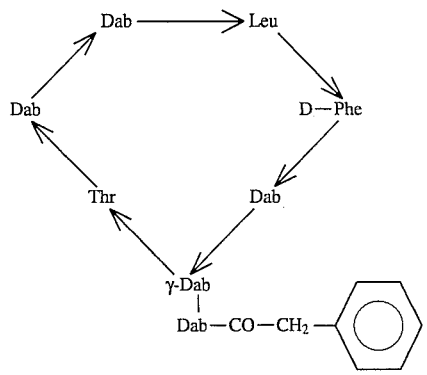

or a physiologically tolerated salt thereof.

6. A method for promoting the absorption of peptides by the mucosa, wherein said method comprises the step of applying to the mucosa an effective amount of at least one compound as claimed in one of claims 2–5, and at least one peptide which has 3 to 51 amino acids and is capable of being absorbed by the mucosa.

7. A pharmaceutical formulation as claimed in claim 1, which comprises a peptide containing 3 to 51 amino acids.

8. A method for promoting the absorption of peptides in application to the mucosa, wherein said method comprises:

applying to the mucosa an effective amount of at least one compound as claimed in one of claims 2–5 and at least one peptide which has 3 to 51 amino acids; and absorption of said peptide by the mucosa.

* * * * *